United States Patent [19]

Miller et al.

[11] Patent Number: 4,510,239
[45] Date of Patent: Apr. 9, 1985

[54] DOUBLE ANTIBODY IMMUNOASSAYS OF ENZYMES SUCH AS PROSTATIC ACID PHOSPHATASE

[75] Inventors: Steven P. Miller, Los Altos; Stella S. M. Quan, Belmont, both of Calif.

[73] Assignee: Beckman Instruments, Inc., Fullerton, Calif.

[21] Appl. No.: 406,644

[22] Filed: Aug. 9, 1982

[51] Int. Cl.$^3$ ............................................. G01N 33/54
[52] U.S. Cl. ........................................ 435/7; 435/21; 435/810; 436/540; 436/548; 436/808
[58] Field of Search ............................. 435/7, 21, 810; 436/540, 548, 808

[56] References Cited

U.S. PATENT DOCUMENTS 4,248,964 2/1981 McDonald ....................... 436/540 X
4,267,272 5/1981 Josephson ......................... 435/21 X
4,298,592 11/1981 Lin ....................................... 436/540

OTHER PUBLICATIONS

B. K. Choe et al., Clin. Chem., 26(13), 1854–1859, (1980).
Chemical Abstracts, 97: 211552x, (1982).

Primary Examiner—Sidney Marantz
Attorney, Agent, or Firm—R. J. Steinmeyer; R. R. Meads; R. S. Frieman

[57] ABSTRACT

A method, kit and a solution for assaying enzyme, such as prostate acid phosphatase (PAP), in a sample. The sample is contacted with a first antibody ($Ab_1$) against the enzyme and incubated. The resulting $Ab_1$-enzyme complex is contacted with a second antibody ($Ab_2$) specific for $Ab_1$. The resulting $Ab_2$-$Ab_1$-enzyme complex precipitates out of the medium. The precipitated complex is separated and solubilized with a pH controlled solution of gamma globulin. The resulting solution is then assayed for enzyme activity.

38 Claims, No Drawings

DOUBLE ANTIBODY IMMUNOASSAYS OF ENZYMES SUCH AS PROSTATIC ACID PHOSPHATASE

BACKGROUND OF THE INVENTION

1. Field of the Invention

This invention relates to a method for assaying an enzyme in a sample and a kit for use therein. More particularly, this invention relates to a kinetic method for assaying prostate acid phosphatase (PAP) in a sample and to a kit for use therein.

2. Description of the Prior Art

Methods for the assay of acid phosphatase and prostatic acid phosphatase (PAP) have been reported (1–5). Choe et al. (1) disclose an immunoenzyme assay for human PAP wherein anti-PAP~PAP complexes are precipitated with a 100% saturated solution of $(NH_4)_2SO_4$. After removing a supernatant, pellets are dissolved in acetate or citrate buffer, pH 5.0. The enzyme assay is initiated by the addition of p-nitrophenylphosphate and the enzyme reaction is stopped by the addition of sodium hydroxide.

Choe et al. (2) and Ly et al. (3) disclose an immunoassisted assay (IAA) for PAP basically consisting of the following reaction sequence:

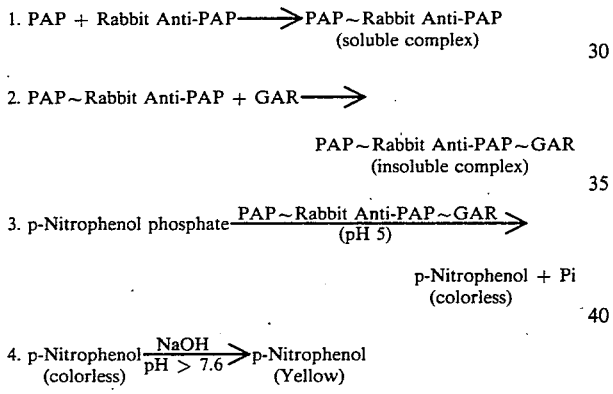

wherein GAR denotes goat anti-rabbit Ig and Pi denotes inorganic phosphate.

The above immunoassays suffer from various pitfalls, including, the requirement of a sample blank; a time-consuming procedure; and the requirement of a potentially hazardous alkaline solution (NaOH) to stop the reaction and color development of the chromophore (p-nitrophenol).

Sanders et al. (4) and Quan et al. (5) disclose a kinetic determination method for acid phosphatase with α-naphthyl phosphate as substrate and a diazonium salt for color development. Quan et al. also disclose a method for indirectly calculating PAP acitivity. In addition, Quan et al. also disclose that better sensitivity and specificity can be achieved by activating the PAP and suppressing the non-prostatic acid phosphatase with 1,5-pentanediol, and that better solubility of the azo dye complex is achieved by the addition of a detergent, namely Brij-35.

The methods of Sanders et al. and Quan et al. suffer from various pitfalls including the instability of the complete reagent for the kinetic acid phosphatase determination which necessitates the use of the reagent blank, the interaction of plasma and serum components and diazonium salts which makes advisable the use of a sample blank measured in the absence of substrate for every determination, and the inability to directly measure PAP.

It would be advantageous to have a kinetic assay for the determination of PAP which eliminates most, if not all, of the disadvantages present in the above-described methodology.

SUMMARY OF THE INVENTION

In accordance with the present invention, there is provided an improved kinetic method for directly assaying prostatic acid phosphatase (PAP) as well as a kit for use therein. The method of the instant invention does not require a sample blank, the assay time is relatively short, does not require the use of a potentially hazardous solution to stop the reaction and color development of the chromophore, and avoids any interaction between plasma components and the diazonium salts employed. More particularly, the kinetic method for assaying PAP of the instant invention comprises:

(a) contacting a sample with a first antibody ($Ab_1$) against PAP, wherein the amount of $Ab_1$ employed is at least sufficient to bind substantially all of the PAP in the sample;

(b) incubating a first medium containing $Ab_1$ and PAP for a time at least sufficient to enable $Ab_1$ to bind to substantially all of the PAP to form $Ab_1$~PAP complexes;

(c) contacting the $Ab_1$~PAP complexes with a second antibody ($Ab_2$) capable of recognizing $Ab_1$, wherein the amount of $Ab_2$ employed is at least sufficient to bind substantially all of the $Ab_1$~PAP complexes and form a precipitate with substantially all of the complexes;

(d) incubating a second medium containing $Ab_2$ and $Ab_1$~PAP complexes for a time at least sufficient to enable (i) the $Ab_2$ to bind to substantially all of said $Ab_1$~PAP complexes and (ii) substantially all of the $Ab_2$~$Ab_1$~PAP complexes to precipitate out of the second medium;

(e) separating the precipitated $Ab_2$~$Ab_1$~PAP complexes from the second medium;

(f) contacting the separated, precipitated $Ab_2$~$Ab_1$~PAP complexes with a solution (i) having a pH ≦ about 3 and (ii) comprising γ-globulin in an amount at least sufficient to prevent substantially any precipitation of $Ab_2$~$Ab_1$~PAP complexes at a pH suitable for formation of the precipitate, thereby forming a resulting solution;

(g) contacting the resulting solution with a non-interfering, water soluble detergent capable of further enhancing the solubility of constituents present at any time in step (i);

(h) contacting the detergent containing resulting solution with a water soluble n-alcohol having at least one terminal hydroxyl group and capable of participating in a transphosphorylation reaction, the alcohol being employed in an amount such that it is not a rate limiting factor in a reaction between a substrate and the alcohol in the presence of PAP;

(i) contacting the alcohol and detergent containing resulting solution with a buffered reaction medium comprising the substrate, a reagent capable of reacting with a product of the alcohol, substrate, PAP reaction to produce a detectable product, and a buffer having a pH compatible with an assay of PAP activity; and (j) kinetically measuring the detectable product of step (i).

In addition, the instant invention comprises a kit for kinetically assaying PAP in a sample comprising:
(a) a first component comprising a first antibody ($Ab_1$) against PAP, wherein the amount of $Ab_1$ therein is at least sufficient to bind substantially all of the PAP in said sample to form $Ab_1 \sim PAP$ complexes;
(b) a second component comprising a second antibody ($Ab_2$) capable of recognizing $Ab_1$ wherein the amount of $Ab_2$ therein is at least sufficient to bind substantially all of the $Ab_1 \sim PAP$ complexes to form $Ab_2 \sim Ab_1 \sim PAP$ complexes and form a precipitate with substantially all of the complexes;
(c) a third component comprising a solution (i) having a pH $\leq$ about 3 and (ii) comprising $\gamma$-globulin in an amount at least sufficient to prevent substantially any precipitation of $Ab_2 \sim Ab_1 \sim PAP$ complexes at a pH suitable for formation of the precipitate;
(d) a fourth component comprising a non-interfering, water soluble detergent;
(e) a fifth component comprising a water soluble n-alcohol having at least one terminal hydroxyl group and capable of participating in a transphosphorylation reaction, the alcohol therein being in an amount such that it is not a rate limiting factor in a reaction between a substrate and the alcohol in the presence of PAP;
(f) a sixth component comprising a buffered reaction medium comprising the substrate, a reagent capable of reacting with a product of the alcohol, substrate, PAP reaction to produce a detectable product, and a buffer having a pH compatible with an assay of PAP activity.

The instant invention also comprises a solution (i) having a pH $\leq 3$ and (ii) comprising $\gamma$-globulin in an amount at least sufficient to prevent substantially any precipitation of $Ab_2 \sim Ab_1 \sim PAP$ complexes at a pH suitable for formation of the precipitate.

Still other features and attendant advantages of the present invention will become apparent to those skilled in the art from a reading of the following detailed description of the preferred embodiment.

DETAILED DESCRIPTION OF THE PREFERRED EMBODIMENT

Virtually any $Ab_1$ against PAP which does not totally inhibit or inactivate PAP's enzymatic activity can be employed in the instant invention. Preferably, $Ab_1$ does not decrease PAP's enzymatic activity by more than 50%, more preferably by more than 30%, and optimally by more than 20%.

$Ab_1$ can be present in either antiserum or can be purified. The amount of $Ab_1$ employed is not critical but preferably is present in a quantity sufficient to titer about 75 IU PAP.

Virtually any $Ab_2$ capable of recognizing $Ab_1$ can be employed in the instant invention. Preferably, $Ab_2$ is goat anti-rabbit IgG.

$Ab_2$ can be present in either antiserum or can be purified. The amount of $Ab_2$ employed should be in molar excess of the amount of $Ab_1$ employed. Preferably the molar ratio of $Ab_1$ to $Ab_2$ is from about 1:3 to about 1:10, more preferably from about 1:4 to about 1:6, and optimally about 1:5.

The solution employed in the kinetic method for assaying PAP of the instant invention has a pH of $\leq$ about 3 and comprises $\gamma$-globulin in an amount at least sufficient to prevent substantially any precipitation of $Ab_2 \sim Ab_1 \sim PAP$ complexes at a pH suitable for formation of the precipitate. The solution preferably has a pH of from about 2 to about 2.8, more preferably from about 2.5 to about 2.7, and optimally about 2.53. Any solution capable of attaining this pH can be employed in the present invention. Such solutions include, but are not limited to, phosphoric acid, citric acid, formic acid, and succinic acid. Preferably the solution is a citric acid solution.

Virtually any $\gamma$-globulin can be employed in the instant invention. The $\gamma$-globulin must be derived from the same species which produced $Ab_1$. Preferably, the $\gamma$-globulin is a rabbit $\gamma$-globulin.

The $\gamma$-globulin can be present in either antiserum or can be purified. Preferably, the $\gamma$-globulin is purified and employed in the form of immunoglobulin.

The amount of $\gamma$-globulin employed should be in molar excess of the amount of $Ab_1$ employed. Preferably the molar ratio of Ab, to $\gamma$-globulin is from about 1: greater than 1 to about 1:5 and more preferably about 1:2.

Virtually any non-interfering, water soluble detergent which is capable of further enhancing the solubility of constituents present at any time in the enzymatic reaction medium can be employed in the instant invention. Of particular importance, the detergent should be capable of enhancing the solubility of the chromophore and immunoglobulins present in the reaction medium. Typical detergents include, but are not limited to, Brij-35 and Triton X-100. Preferably, the detergent is Brij-35.

Virtually any water soluble n-alcohol having at least one terminal hydroxyl group and capable of participating in a transphorylation reaction can be employed in the instant invention. The amount of alcohol employed should be such that it is not a rate limiting factor in a reaction between a substrate and the alcohol in the presence of PAP. The water soluble, n-alcohol is preferably an alkyl diol having 2 to 5 carbon atoms and more preferably from 3 to 5 carbon atoms. Typical alkyl diols capable of use in the instant invention include, but are not limited to, 1,2-propanediol, 1,3-propanediol, 1,2-butanediol, 1,3-butanediol, 1,4-butanediol, and 1,5-pentanediol. Optimally, the alcohol is 1,5-pentanediol.

Virtually any buffered reaction medium comprising a substrate, reagent capable of reacting with a product of the alcohol, substrate, PAP reaction to produce a detectable product, and a buffer having a pH compatible with an assay of PAP activity can be employed in the instant invention. The buffered reaction medium preferably has a pH of from about 5 to about 5.5, more preferably from about 5.3 to about 5.4, and optimally about 5.35.

Virtually any buffer having a pH compatible with an assay of PAP activity can be employed in the instant invention. Buffers which can be employed in the instant invention include, but are not limited to, citrate, succinate, and acetate buffers. Preferably the buffer is a citrate buffer.

Virtually any substrate capable of reacting with an alcohol in the presence of PAP can be employed in the instant invention. Such substrates include, but are not limited to, $\alpha$-naphthyl phosphate, $\beta$-naphthyl phosphate, and glycerol phosphate. Preferably, the substrate is selected from the group consisting of α-naphthyl phosphate and β-naphthyl phosphate. More preferably, the substrate is α-naphthyl phosphate.

The solutions which comprise $Ab_1$ and $Ab_2$ can optionally further comprise a bulking agent and/or an anti-microbial agent. Virtually any bulking agent can be used in the instant invention. Typical bulking agents include, but are not limited to, mannitol, sucrose, and lactose. The bulking agent preferably is mannitol.

Virtually any anti-microbial agent can be employed in the instant invention. Typical anti-microbial agents include, but are not limited to, thimerosal, sodium azide, and Hyamine 3500. The anti-microbial agent is preferably thimerosal.

Methods for making the various components as well as the various constituents employed therein are well known to those skilled in the art and, accordingly, need not be elaborated upon herein.

In performing the kinetic method for assaying PAP of the instant invention, the first medium containing $Ab_1$ and PAP must be incubated for a time at least sufficient to enable the $Ab_1$ to bind to substantially all of the PAP to form $Ab_1 \sim PAP$ complexes. Preferably, $Ab_1$ and PAP are incubated for at least 10 minutes. More preferably the $Ab_1$ and PAP are incubated for $30 \pm 33\%$ minutes and optimally for about $30 \pm 15\%$ minutes.

The second medium containing $Ab_2$ and the $Ab_1 \sim PAP$ complexes must be incubated for a time at least sufficient to enable (i) the $Ab_2$ to bind to substantially all of the $Ab_1 \sim PAP$ complexes to form $Ab_2 \sim Ab_1 \sim PAP$ complexes and (ii) substantially all of the $Ab_2 \sim Ab_1 \sim PAP$ complexes to precipitate out of the second medium. This incubation procedure should be for at least about 10 minutes and is preferably performed for about $30 \pm 33\%$ minutes and more preferably about $30 \pm 15\%$ minutes.

The following examples are provided for the purpose of further illustration only and are not intended to be limitations on the disclosed invention.

EXAMPLE 1

TABLE I

PAP Kinetic Kit Formulation

| Component | Constituent | Preferred | More Preferred | Optimal |
|---|---|---|---|---|
| $Ab_1$ Solution | Rabbit antiserum, $Ab_1$, mg/ml | 2±20% | 2±15% | 2±5% |
| | citric acid, mmol/L | 5.4±15% | 5.4±10% | 5.4±5% |
| | sodium citrate, mmol/L | 21.7±15% | 21.7±10% | 21.7±5% |
| | bulking agent | optional | optional | 10 mg/ml mannitol |
| | anti-microbial agent | optional | optional | ~0.005 to ~0.01 mg/ml thimerosal |
| $Ab_2$ Solution | goat anti-rabbit antiserum, IgG, mg/ml | 10±20% | 10±15% | 10±5% |
| | citric acid, mmol/L | 7.8±15% | 7.8±10% | 7.8±5% |
| | sodium citrate, mmol/L | 20.5±15% | 20.5±10% | 20.5±5% |
| | bulking agent | optional | optional | 10 mg/ml mannitol |
| | anti-microbial agent | optional | optional | ~0.005 to ~0.1 |

TABLE I-continued

PAP Kinetic Kit Formulation

| Component | Constituent | Preferred | More Preferred | Optimal |
|---|---|---|---|---|
| | agent | | | thimerosal |
| Dissolution Reagent | citric acid, mmol/L | 20±15% | 20±10% | 20±5% |
| | rabbit γ-globulin, mg/ml | 0.625±15% | 0.625±10% | 0.625±5% |
| | pH | 2.53±15% | 2.53±10% | 2.53±5% |
| Detergent | Brij-35, mmol/L | 4±15% | 4±10% | 4±5% |
| Alcohol | 1,5-pentanediol, mmol/L | 150±15% | 150±15% | 150±5% |
| Buffered Reaction Medium | α-naphthyl phosphate, mmol/L | 5.8±15% | 5.8±10% | 5.8±5% |
| | fast red TR, mmol/L | 3.6±15% | 3.6±10% | 3.6±5% |
| | citrate, mmol/L | 75±15% | 75±10% | 75±5% |
| | pH | 5.35±15% | 5.35±10% | 5.35±5% |

EXAMPLE 2

PAP Kinetic Assay Procedure (a) Label test tubes for test specimen and appropriate controls.

(b) Add to each tube:
0.5 ml sample
0.5 ml $Ab_1$
Vortex tubes for 2-5 seconds.
Incubate at 20°-25° C. for 30-60 minutes.

(c) Add to each tube: 0.5 ml $Ab_2$
Vortex tubes for 2-5 seconds.
Incubate at 20°-25° C. for 30-60 minutes.

(d) Add to each tube: 0.5 ml saline
Vortex tubes for 2-5 seconds.
Centrifuge at 2600-3000 rpm for 20 minutes.

(e) Decant. Do not disturb precipitate.

(f) Add to each tube: 0.5 ml dissolution reagent. Vortex tubes for 90 seconds to dissolve pellet. THE SOLUTION IS USED AS "SAMPLE" FOR THE FOLLOWING STEP.

(g) Pipette 2 ml acid phosphatase reagent to each cuvette. Equilibrate to 30° C. or 37° C.

(h) Add 0.2 ml "SAMPLE" and mix, at timed intervals. Incubate at 30° C. or 37° C. Record the absorbance change at 405 nm at 5 and 10 minutes.

(i) Compute the absorbance change per minute at 405 nm between 5 and 10 minutes after sample addition.

(j) Calculate PAP activity:

$$IU = \frac{\Delta A}{T} \times \frac{TV}{SV} \times \frac{1}{10^{-6} \times \epsilon} \times 1000$$

Where
ΔA = absorbance change between readings
T = time between readings in minutes
TV = total volume in ml
SV = sample volume in ml
ε = molar absorptivity of α-naphthyl-Fast Red TR complex at 405 nm.
ε = $15.1 \times 10^6$ cm²/mole

EXAMPLE 3

Precision Study

Using the procedure of Example 2, the within-run precision was determined with normal patient sera pools, patient sera pools spiked with PAP and an abnormal serum control.

Day-to-day precision was performed over a period of 7 days with normal patient sera pools, patient sera pools spiked with PAP and an abnormal serum control, which were aliquoted and kept frozen at $-70°$ C. until assayed for PAP activity. Each sample was run in triplicate every day and the mean values are set forth in Table II.

TABLE II

| Sample | n | Range (U/L) | Mean (U/L) | S.D. (U/L) | C.V. (%) |
|---|---|---|---|---|---|
| Run-to-Run | | | | | |
| Level I | 18 | 1.9–2.3 | 2.2 | 0.14 | 6.4 |
| Level II | 18 | 37.3–39.8 | 38.7 | 0.81 | 2.1 |
| Level III | 18 | 68.8–76.1 | 72.6 | 2.00 | 2.8 |
| Day-to-Day | | | | | |
| Level I | 7 | 0.9–1.2 | 1.04 | 0.10 | 9.94 |
| Level II | 7 | 4.1–4.4 | 4.29 | 0.12 | 2.83 |
| Level III | 7 | 41.0–41.6 | 41.14 | 0.21 | 0.52 |

EXAMPLE 4

Correlation Study

The performance of the improved kinetic PAP test procedure of this invention, as embodied in Example 2, was compared with a commercially available radioimmunoassay kit. The results obtained are summarized in Table III.

TABLE III

| | n | Slope | Intercept | Correlation Coefficient |
|---|---|---|---|---|
| Kinetic PAP vs. PAP RIA | 39 | 0.53 | −0.71 | 0.98 |

$$IAA(IU) = 0.53 RIA(mg/ml) - 0.71$$

Table III indicates that a very good correlation was obtained between the two methods.

EXAMPLE 4

Linearity Study

The linearity of the method of this invention, as embodied in Example 2, was tested by assaying serial dilutions of an underreconstituted abnormal serum control, using an acidified normal serum pool of known PAP activity as diluent. The PAP activity has been corrected for diluent sample activity. The results are set forth in Table IV.

TABLE IV

| Sample Activity (U/L) | $\frac{1}{\text{Dilution}} \times 100$ |
|---|---|
| 0.30 | 0.39 |
| 0.59 | 0.78 |
| 1.20 | 1.56 |
| 4.72 | 6.25 |
| 9.58 | 12.50 |
| 19.17 | 25 |
| 39.34 | 50 |

TABLE IV-continued

| Sample Activity (U/L) | $\frac{1}{\text{Dilution}} \times 100$ |
|---|---|
| 74.74 | 100 |

The data set forth in Table IV indicate that the response of the assay is linear for serum samples with activity up to 75 IU.

The improved double antibody immunoassay test procedure for PAP measurements of the instant invention is simple, rapid, precise, sensitive and specific. This assay offers numerous advantages. For example, neither sample blank nor the addition of alkali to stop the reaction is needed. In addition, the instant assay entails a much shorter assay time. More particularly, the time required from the dissolution of the PAP-immunoprecipitation complex until the determination of the assay is reduced from one hour to about 10 minutes. The methodology of the invention also offers a wider applicability of the IAA-PAP test procedure and provides an alternative to RIA for measurement of PAP. Furthermore, the high linearity (namely, up to 75 IU) of the test of the instant invention means that one will encounter fewer dilutions and repeats with the methodology of the invention. It is also significant to note that the methodology of the instant invention is kinetic and can be easily automated. The problem of interaction between plasma and serum components and diazonium salts is also eliminated by the methodology of this invention.

The method of the instant invention can also be employed to assay any enzyme of interest. Such a methodology of general applicability comprises the following steps:

(a) contacting a sample with a first antibody ($Ab_1$) against the enzyme of interest, wherein the amount of $Ab_1$ employed is at least sufficient to bind substantially all of the enzyme in the sample;

(b) incubating a first medium containing $Ab_1$ and the enzyme for a time at least sufficient to enable the $Ab_1$ to bind to substantially all of the enzyme to form $Ab_1 \sim$ enzyme complexes;

(c) contacting the $Ab_1 \sim$ enzyme complex with a second antibody ($Ab_2$) capable of recognizing $Ab_1$, wherein the amount of $Ab_2$ employed is at least sufficient to bind substantially all of the $Ab_1 \sim$ enzyme complexes and form a precipitate with substantially all of the complexes;

(d) incubating a second medium containing the $Ab_2$ and the $Ab_1 \sim$ enzyme complexes for a time at least sufficient to enable (i) the $Ab_2$ to bind to substantially all of the $Ab_1 \sim$ enzyme complexes to form $Ab_2 \sim Ab_1 \sim$ enzyme complexes and (ii) substantially all of the $Ab_2 \sim Ab_1 \sim$ enzyme complexes to precipitate out of the second medium;

(e) separating the precipitated $Ab_2 \sim Ab_1 \sim$ enzyme complexes from the second medium;

(f) contacting the separated, precipitated $Ab_2 \sim Ab_1 \sim$ enzyme complexes with a solution (i) having a pH at least sufficient to solubilize substantially all of the $Ab_2 \sim Ab_1 \sim$ enzyme complexes and (ii) comprising $\gamma$-globulin in an amount at least sufficient to prevent substantially any precipitation of $Ab_2 \sim Ab_1 \sim$ enzyme complexes at a pH suitable for formation of the precipitate, thereby forming a resulting solution;

(g) contacting a sufficient amount of the resulting solution with a reaction medium capable of being used to assay the enzyme; and (h) assaying the enzyme.

If necessary to maintain the solution formed in step (g) at the optimal pH of the enzyme being assayed, the reaction medium should be buffered at this pH.

Preferably, after step (e) and in or before step (g) a non-interfering, water soluble detergent is employed to further enhance the solubility of constituents present at any time in step (g).

It is also preferred that the reaction medium be a kinetic reaction medium and that the enzyme be assayed kinetically.

To further reduce the time required for performing the assay of the instant invention, one can simultaneously perform steps (a) through (g) of the above procedure. In such event, $Ab_1$ should be selected from a group consisting of monoclonal and polyclonal antibody and $Ab_2$ should be selected from a group consisting of monoclonal and polyclonal antibody, provided that at least one of $Ab_1$ and $Ab_2$ is a monoclonal antibody.

A kit capable of use in the above generalized enzyme procedure comprises:

(a) a first component comprising a first antibody ($Ab_1$) against the enzyme, wherein the amount of $Ab_1$ therein is at least sufficient to bind substantially all of the enzyme in the sample to form $Ab_1 \sim$ enzyme complexes;

(b) a second component comprising a second antibody ($Ab_2$) capable of recognizing $Ab_1$, wherein the amount of $Ab_2$ therein is at least sufficient to bind substantially all of the $Ab_1 \sim$ enzyme complexes to form $Ab_2 \sim Ab_1 \sim$ enzyme complexes and form a precipitate with substantially all of the complexes;

(c) a third component comprising a solution (i) having a pH at least sufficient to solubilize precipitated $Ab_2 \sim Ab_1 \sim$ enzyme complexes and (ii) comprising γ-globulin in an amount at least sufficient to prevent substantially any precipitation of $Ab_2 \sim Ab_1$-~enzyme complexes at a pH suitable for formation of the precipitate; and (d) a fourth component comprising a reaction medium capable of being used to assay the enzyme.

The kit can further optionally comprise a non-interfering, water soluble detergent.

Preferably, the reaction medium employed in the kit is a kinetic reaction medium.

If one desires to combine the first and second components into a single component, then $Ab_1$ should be selected from the group consisting of monoclonal and polyclonal antibodies and $Ab_2$ should be selected from a group consisting of monoclonal and polyclonal antibodies, provided that at least one of $Ab_1$ and $Ab_2$ is a monoclonal antibody.

Based on this disclosure, many other modifications and ramifications will naturally suggest themselves to those skilled in the art. These are intended to be comprehended as within the scope of this invention.

BIBLIOGRAPHY

1. Choe et al., *Proceedings of the Society for Experimental Biology and Medicine*, 162:396–400 (1979).
2. Choe et al., *Clin. Chem.*, 26 (13):1854–1859 (1980).
3. Ly et al., *Clin. Chem.*, 27 (6):1064 (1981).
4. Sanders et al., *Clinica Chimica Acta*, 89:421–427 (1978).
5. Quan et al., *Clin. Chem.*, 27 (16):1062 (1981).

The embodiments of the invention in which an exclusive property or privilege is claimed are defined as follows:

1. A method for assaying an enzyme in a sample comprising:

(a) contacting said sample with a first antibody ($Ab_1$) against said enzyme, wherein the amount of $Ab_1$ employed is at least sufficient to bind substantially all of said enzyme in said sample;

(b) incubating a first medium containing said $Ab_1$ and said enzyme for a time at least sufficient to enable said $Ab_1$ to bind to substantially all of said enzyme to form $Ab_1 \sim$ enzyme complexes;

(c) contacting said $Ab_1 \sim$ enzyme complex with a second antibody ($Ab_2$) capable of recognizing $Ab_1$, wherein the amount of $Ab_2$ employed is at least sufficient to bind substantially all of said $Ab_1 \sim$ enzyme complexes and form a precipitate with substantially all of said complexes;

(d) incubating a second medium containing said $Ab_2$ and said $Ab_1 \sim$ enzyme complexes for a time at least sufficient to enable (i) said $Ab_2$ to bind to substantially all of said $Ab_1 \sim$ enzyme complexes to form $Ab_2 \sim Ab_1 \sim$ enzyme complexes and (ii) substantially all of said $Ab_1 \sim Ab_2 \sim$ enzyme complexes to precipitate out of said second medium;

(e) separating said precipitated $Ab_2$-$Ab_1$-enzyme complexes from said second medium;

(f) contacting said separated, precipitated $Ab_2 \sim Ab_1$-~enzyme complexes with a solution (i) having a pH at least sufficient to solubilize substantially all of said $Ab_2 \sim Ab_1 \sim$ enzyme complexes and (ii) comprising γ-globulin in an amount at least sufficient to prevent substantially any precipitation of $Ab_2 \sim Ab_1 \sim$ enzyme complexes at a pH suitable for formation of said precipitate, thereby forming a resulting solution;

(g) contacting a sufficient amount of said resulting solution with a reaction medium, to thereby form a reaction environment containing various constituents, wherein said reaction medium is capable of being used to assay said enzyme; and (h) assaying said enzyme.

2. The method of claim 1 wherein after step (e) and in or before step (g) a non-interfering, water soluble detergent is added to further enhance the solubility of constituents present at any time in step (g).

3. The method of claim 1 wherein said reaction medium is a kinetic reaction medium and said enzyme is assayed kinetically.

4. The method of claim 1 wherein after step (e) and in or before step (g) a non-interfering, water soluble detergent is added to further enhance the solubility of constituents present at any time in step (g), said reaction medium is a kinetic reaction medium, and said enzyme is assayed kinetically.

5. The method of claim 1 wherein steps (a) through (d) are conducted simultaneously and said $Ab_1$ is selected from the group consisting of monoclonal and polyclonal antibodies and said $Ab_2$ is selected from the group consisting of monoclonal and polyclonal antibodies.

6. The method of claim 5 wherein after step (e) and in or before step (g) a non-interfering, water soluble detergent is added to further enhance the solubility of constituents present at any time in step (g).

7. The method of claim 5 wherein said reaction medium is a kinetic reaction medium and said enzyme is assayed kinetically.

8. The method of claim 5 wherein after step (e) and in or before step (g) a non-interfering, water soluble detergent is added to further enhance the solubility of constituents present at any time in step (g), said reaction medium is a kinetic reaction medium, and said enzyme is assayed kinetically.

9. A kinetic method for assaying prostate acid phosphatase (PAP) in a sample comprising:
  (a) contacting said sample with a first antibody ($Ab_1$) against said PA, wherein the amount of $Ab_1$ employed is at least sufficient to bind substantially all of said PAP in said sample;
  (b) incubating a first medium containing said $Ab_1$ and said PAP for a time at least sufficient to enable said $Ab_1$ to bind to substantially all of said PAP to form $Ab_1 \sim PAP$ complexes;
  (c) contacting said $Ab_1 \sim PAP$ complexes with a second antibody ($Ab_2$) capable of recognizing $Ab_1$, wherein the amount of $Ab_2$ employed is at least sufficient to bind substantially all of said $Ab_1 \sim PAP$ complexes and form a precipitate with substantially all of said complexes;
  (d) incubating a second medium containing said $Ab_2$ and said $Ab_1 \sim PAP$ complexes for a time at least sufficient to enable (i) said $Ab_2$ to bind to substantially all of said $Ab_1 \sim PAP$ complexes to form $Ab_2 \sim Ab_1 \sim PAP$ complexes and (ii) substantially all of said $Ab_2 \sim Ab_1 \sim PAP$ complexes to precipitate out of said second medium;
  (e) separating said precipitated $Ab_2 \sim Ab_1 \sim PAP$ complexes from said second medium;
  (f) contacting said separated, precipitated $Ab_2 \sim Ab_1 \sim PAP$ complexes with a solution (i) having a pH $\leq$ about 3 and (ii) comprising $\gamma$-globulin in an amount at least sufficient to prevent substantially any precipitation of $Ab_2 \sim Ab_1 \sim PAP$ complexes at a pH suitable for formation of said precipitate, thereby forming a resulting solution;
  (g) contacting said resulting solution with a non-interfering, water soluble detergent capable of further enhancing the solubility of constituents present at any time in step (i);
  (h) contacting said detergent containing resulting solution with a water soluble n-alcohol having at least one terminal hydroxyl group and capable of participating in a transphosphorylation reaction, said alcohol being employed in an amount such that it is not a rate limiting factor in a reaction between a substrate and said alcohol in the presence of said PAP;
  (i) contacting said alcohol and detergent containing resulting solution with a buffered reaction medium comprising said substrate, a reagent capable of reacting with a product of said alcohol, substrate, PAP reaction to produce a detectable product, and a buffer having a pH compatible with an assay of PAP activity; and
  (j) kinetically measuring said detectable product of step (i).

10. The method of claim 9 wherein said $Ab_1$ is rabbit $Ab_1$; said $Ab_2$ is goat anti-rabbit IgG; said solution has a pH of from about 2 to about 2.8 and is selected from the group consisting of phosphoric acid, citric acid, formic acid, and succinic acid solutions containing said $\gamma$-globulin, wherein said $\gamma$-globulin is rabbit $\gamma$-globulin; said detergent is selected from the group consisting of Brij-35 and Triton X-100; said water soluble n-alcohol is an alkyl diol having 2 to 5 carbon atoms; said buffered reaction medium has a pH of from about 5 to about 5.5 and is buffered by a buffer selected from the group consisting of citrate, succinate and acetate buffers; and said substrate is selected from the group consisting of glycerol phosphate, $\alpha$-naphthyl phosphate, and $\beta$-naphthyl phosphate.

11. The method of claim 10 wherein said solution has a pH of from about 2.5 to about 2.7 and is a citric acid solution containing said rabbit $\gamma$-globulin, said alkyl diol contains from 3 to 5 carbon atoms; said buffered reaction medium has a pH of from about 5.3 to about 5.4; said substrate solution is selected from said group consisting of $\alpha$-naphthyl phosphate and $\beta$-naphthyl phosphate; and said reagent comprises a diazonium salt.

12. The method of claim 11 wherein said alkyl diol is selected from the group consisting of 1,2-propanediol, 1,3-propanediol, 1,2-butanediol, 1,3-butanediol, 1,4-butanediol, and 1,5-pentanediol; and wherein said diazonium salt is selected from the group consisting of fast garnet GBC salt, fast blue B salt, naphthanyl diazo red RC, diazotized p-nitroaniline, fast red ITR salt, fast red TR salt, and hexazotised p-rosaniline salt.

13. The method of claim 12 wherein said solution has a pH of about 2.53; said detergent is Brij-35; said alkyl diol is 1,5-pentanediol; said buffered reaction medium has a pH of about 5.35 and said buffer is citrate buffer; said substrate is $\alpha$-naphthyl phosphate; and said diazonium salt is fast red TR.

14. The method of claim 9 wherein:
  (I) said $Ab_1$ is present in a solution comprising about $5.4 \pm 15\%$ mmol/L citric acid, about $21.7 \pm 15\%$ mmol/L sodium citrate, and about $2 \pm 20\%$ mg/ml rabbit antiserum, $Ab_1$;
  (II) said $Ab_1$ and said PAP are incubated for at least about 10 minutes;
  (III) said $Ab_2$ is present in a solution comprising about $7.8 \pm 15\%$ mmol/L citric acid, about $20.5 \pm 15\%$ mmol/L sodium citrate, and about $10 \pm 20\%$ mg/ml goat anti-rabbit IgG antiserum;
  (IV) said $Ab_2$ and said $Ab_1 \sim PAP$ complexes are incubated for at least about 10 minutes;
  (V) said solution comprises about $20 \pm 15\%$ mM citric acid and about $0.625 \pm 15\%$ mg/ml rabbit $\gamma$-globulin and has a pH of about $2.53 \pm 15\%$;
  (VI) said detergent comprises about $4 \pm 15\%$ mM Brij-35;
  (VII) said alcohol comprises about $150 \pm 15\%$ mM 1,5-pentanediol;
  (VIII) said buffered reaction medium comprises about $5.8 \pm 15\%$ mM $\alpha$-naphthyl phosphate, about $3.6 \pm 15\%$ mM fast red TR, about $75 \pm 15\%$ mM citrate, and has a pH of about $5.35 \pm 15\%$; and
  (IX) said kinetic measurement is made at about $10 \pm 10\%$ minutes after commencement of step (i).

15. The method of claim 14 wherein:
  (I) said $Ab_1$ solution comprises about $5.4 \pm 10\%$ mmol/L citric acid, about $21.7 \pm 10\%$ mmol/L sodium citrate, and about $2 \pm 15\%$ mg/L rabbit antiserum, $Ab_1$;
  (II) said $Ab_1$ and said PAP are incubated for about $30 \pm 33\%$ minutes;
  (III) said $Ab_2$ solution comprises about $7.8 \pm 10\%$ mmol/L citric acid, about $20.5 \pm 10\%$ mmol/L sodium citrate, and about 10±15% mg/ml goat anti-rabbit IgG antiserum;

(IV) said $Ab_2$ and said $Ab_1 \sim PAP$ complexes are incubated for about 30±33% minutes;

(V) said solution comprises about 20±10% mM citric acid and about 0.625±10% mg/ml rabbit γ-globulin and has a pH of about 2.53±10%;

(VI) said detergent comprises about 4±10% mM Brij-35;

(VII) said alcohol comprises about 150±10% mM 1,5-pentanediol;

(VIII) said buffered reaction medium comprises about 5.8±10% mM α-naphthyl phosphate, about 3.6±10% mM fast red TR, about 75±10% mM citrate, and has a pH of about 5.35±10%; and (IX) said kinetic measurement is made at about 10±25% minutes after commencement of step (i).

16. The method of any one of claims 14 or 15 wherein said $Ab_1$ and $Ab_2$ solutions further comprise at least one composition selected from the group consisting of bulking agents and anti-microbial agents.

17. The method of any one of claims 14 or 15 wherein said $Ab_1$ and $Ab_2$ solutions further comprise at least one composition selected from the group consisting of bulking agents and anti-microbial agents, wherein said bulking agents are selected from the group consisting of mannitol, sucrose, and lactose; and said anti-microbial agents are selected from the group consisting of thimerosal, sodium azide, and hyamine 3500.

18. The method of any one of claims 14 or 15 wherein said $Ab_1$ and $Ab_2$ solutions further comprise mannitol and thimerosal.

19. The method of claim 15 wherein:

(I) said $Ab_1$ solution comprises about 5.4±5% mmol/L citric acid, about 21.7±5% mmol/L sodium citrate, about 2±5% mg/l rabbit antiserum, $Ab_1$, about 10 mg/ml±15% mannitol, and from about 0.005 to about 0.1 mg/ml thimerosal;

(II) said $Ab_1$ and said PAP are incubated for about 30±15% minutes;

(III) said $Ab_2$ solution comprises about 7.8±5% mmol/L citric acid, about 20.5±5% mmol/L sodium citrate, about 10±5% mg/ml goat anti-rabbit IgG antiserum; about 10 mg/ml±100% mannitol, and from about 0.005 to about 0.1 mg/ml thimerosal;

(IV) said $Ab_2$ and said $Ab_1 \sim PAP$ complexes are incubated for about 30±15% minutes;

(V) said solution comprises about 20±5% mM citric acid and about 0.625±5% mg/ml rabbit γ-globulin and has a pH of about 2.53±10%;

(VI) said detergent comprises about 4±5% mM Brij-35;

(VII) said alcohol comprises about 150±5% mM 1,5-pentanediol;

(VIII) said buffered reactin medium comprises about 5.8±5% mM α-naphthyl phosphate, about 3.6±5% mM fast red TR, about 75±5% mM citrate, and has a pH of about 5.35±5%; and (IX) said kinetic measurement is made at about 10±25% minutes after commencement of step (i).

20. A kit for assaying an enzyme in a sample comprising: (a) a first component comprising a first antibody ($Ab_1$) against said enzyme, wherein the amount of $Ab_1$ therein is at least sufficient to bind substantially all of said enzyme in said ample to form $Ab_1 \sim$ enzyme complexes; (b) a second component comprising a second antibody ($Ab_2$) capable of recognizing $Ab_1$, wherein the amount of $Ab_2$ therein is at least sufficient to bind substantially all of said $Ab_1 \sim$ enzyme complexes to form $Ab_2 \sim Ab_1 \sim$ enzyme complexes and form a precipitate with substantially all of said complexes;

(c) a third component comprising a solution (i) having a pH at least sufficient to solubilize precipitated $Ab_2 \sim Ab_1 \sim$ enzyme complexes and (ii) comprising γ-globulin in an amount at least sufficient to prevent substantially any precipitation of $Ab_2 \sim Ab_1 \sim$ enzyme complexes at a pH suitable for formation of said precipitate; and (d) a fourth component comprising a reaction medium capable of being used to assay said enzyme.

21. The kit of claim 20 further comprising a non-interfering, water soluble detergent.

22. The kit of claim 20 wherein said reaction medium is a kinetic reaction medium.

23. The kit of claim 20 further comprising a non-interfering, water soluble detergent and wherein said reaction medium is a kinetic reaction medium.

24. The kit of claim 20 wherein the first and second components are combined into a single component and wherein $Ab_1$ is selected from the group consisting of monoclonal and polyclonal antibodies and $Ab_2$ is selected from the group consisting of monoclonal and polyclonal antibodies.

25. The kit of claim 24 further comprising a non-interfering, water soluble detergent.

26. The kit of claim 24 wherein said reaction medium is a kinetic reaction medium.

27. The kit of claim 24 further comprising a non-interfering, water soluble detergent and wherein said reaction medium is a kinetic reaction medium.

28. A kit for kinetically assaying prostate acid phosphatase (PAP) in a sample comprising:

(a) a first component comprising a first antibody ($Ab_1$) against said PAP, wherein the amount of $Ab_1$ therein is at least sufficient to bind substantially all of said PAP in said sample to form $Ab_1 \sim PAP$ complexes;

(b) a second component comprising a second antibody ($Ab_2$) capable of recognizing $Ab_1$ wherein the amount of $Ab_2$ therein is at least sufficient to bind substantially all of said $Ab_1 \sim PAP$ complexes to form $Ab_2 \sim Ab_1 \sim PAP$ complexes and form a precipitate with substantially all of said complexes;

(c) a third component comprising a solution (i) having a pH $\leq$ about 3 and (ii) comprising γ-globulin in an amount at least sufficient to prevent substantially any precipitation of $Ab_2 \sim Ab_1 \sim PAP$ complexes at a pH suitable for formation of said precipitate;

(d) a fourth component comprising a non-interfering, water soluble detergent;

(e) a fifth component comprising a water soluble n-alcohol having at least one terminal hydroxyl group and capable of participating in a transphosphorylation reaction, said alcohol therein being in an amount such that it is not a rate limiting factor in a reaction between a substrate and said alcohol in the presence of said PAP;

(f) a sixth component comprising a buffered reaction medium comprising said substrate, a reagent capable of reacting with a product of said alcohol, substrate, PAP reaction to produce a detectable product, and a buffer having a pH compatible with an assay of PAP activity.

29. The kit of claim 25 wherein said $Ab_1$ is rabbit $Ab_1$; said $Ab_2$ is goat anti-rabbit IgG; said solution has a pH of from about 2 to about 2.8 and is selected from the group consisting of phosphoric acid, citric acid, formic acid, and succinic acid solutions containing said γ-globulin, wherein said γ-globulin is rabbit γ-globulin; said detergent is selected from the group consisting of Brij-35 and Triton X-100; said water soluble n-alcohol is an alkyl diol having 2 to 5 carbon atoms; said buffered reaction medium has a pH of from about 5 to about 5.5 and is buffered by a buffer selected from the group consisting of citrate, succinate and acetate buffers; and said substrate is selected from the group consisting of glycerol phosphate, α-naphthyl phosphate, and β-naphthyl phosphate.

30. The kit of claim 29 wherein said solution has a pH of from about 2.5 to about 2.7 and is a citric acid solution containing said rabbit γ-globulin, said alkyl diol contains from 3 to 5 carbon atoms; said buffered reaction medium has a pH of from about 5.3 to about 5.4; said substrate solution is selected from said group consisting of α-naphthyl phosphate and β-naphthyl phosphate; and said reaction comprises a diazonium salt.

31. The kit of claim 30 wherein said alkyl diol is selected from the group consisting of 1,2-propanediol, 1,3-propanediol, 1,2-butanediol, 1,3-butanediol, 1,4-butanediol, and 1,5-pentanediol; and wherein said diazonium salt is selected from the group consisting of fast garnet GBC salt, fast blue B salt, naphthanyl diazo red RC, diazotized p-nitroaniline, fast red ITR salt, fast red TR salt, and hexazotised p-rosaniline salt.

32. The kit of claim 31 wherein said solution has a pH of about 2.53; said detergent is Brij-35; said alkyl diol is 1,5-pentanediol; said buffered reaction medium has a pH of about 5.35 and said buffer is citrate buffer; said substrate is α-naphthyl phosphate; and said diazonium salt is fast red TR.

33. The kit of claim 28 wherein:
(I) said $Ab_1$ is present in a solution comprising about 5.4±15% mmol/L citric acid, about 21.7±15% mmol/L sodium citrate, and about 2±20% mg/ml rabbit antiserum, $Ab_1$;
(II) said $Ab_2$ is present in a solution comprising about 7.8±15% mmol/L citric acid, about 20.5±15% mmol/L sodium citrate, and about 10±20% mg/ml goat anti-rabbit IgG antiserum;
(III) said solution comprises about 20±15% mM citric acid and about 0.625±15% mg/ml rabbit γ-globulin and has a pH of about 2.53±15%;
(IV) said detergent comprises about 4±15% mM Brij-35;
(V) said alcohol comprises about 150±15% mM 1,5-pentanediol; and
(VI) said buffered reaction medium comprises about 5.8±15% mM α-naphthyl phosphate, about 3.6±15% mM fast red TR, about 75±15% mM citrate, and has a pH of about 5.35±15%.

34. The kit of claim 33 wherein:
(I) said $Ab_1$ solution comprises about 5.4±10% mmol/L citric acid, about 21.7±10% mmol/L sodium citrate, and about 2±15% mg/ml rabbit antiserum $Ab_1$;
(II) said $Ab_2$ solution comprises about 7.8±10% mmol/L citric acid, about 20.5±10% mmol/L sodium citrate, and about 10±15% mg/ml goat anti-rabbit IgG antiserum;
(III) said solution comprises about 20±10% mM citric acid and about 0.625±10% mg/ml rabbit γ-globulin and has a pH of about 2.53±10%;
(IV) said detergent comprises about 4±10% mM Brij-35;
(V) said alcohol comprises about 150±10% mM 1,5-pentanediol; and
(VI) said buffered reaction medium comprises about 5.8±10% mM α-naphthyl phosphate, about 3.6±10% mM fast red TR, about 75±10% mM citrate, and has a pH of about 5.35±10%.

35. The kit of any one of claim 33 or 34 wherein said $Ab_1$ and $Ab_2$ solutions further comprise at least one composition selected from a group consisting of bulking agents and anti-microbial agents.

36. The kit of any one of claim 33 or 34 wherein said $Ab_1$ and $Ab_2$ solutions further comprise at least one composition selected from the group consisting of bulking agents and anti-microbial agents, wherein said bulking agents are selected from the group consisting of mannitol, sucrose, and lactose, and said anti-microbial agents are selected from the group consisting of thimerosal, sodium azide, and hyamine 3500.

37. The kit of any one of claim 33 or 34 wherein said $Ab_1$ and $Ab_2$ solutions further comprise mannitol and thimerosal.

38. The kit of claim 34 wherein:
(I) said $Ab_1$ solution comprises about 5.4±5% mmol/L citric acid, about 21.7±5% mmol/L sodium citrate, about 2±5% mg/l rabbit antiserum, $Ab_1$, about 10 mg/ml±15% mannitol, and from about 0.005 to about 0.1 mg/ml±15% thimerosal;
(II) said $Ab_2$ solution comprises about 7.8±5% mmol/L citric acid, about 20.5±5% mmol/L sodium citrate, about 10±5% mg/ml goat anti-rabbit IgG antiserum, about 10 mg/ml±15% mannitol, and from about 0.005 to about 0.1 mg/ml±15% thimerosal;
(III) said solution comprises about 20±5% mM citric acid and about 0.625±5% mg/ml rabbit γ-globulin and has a pH of about 2.53±10%;
(IV) said detergent comprises about 4±5% mM Brij-35;
(V) said alcohol comprises about 150±5% mM 1,5-pentanediol; and
(VI) said buffered reactin medium comprises about 5.8±5% mM α-naphthyl phosphate, about 3.6±5% mM fast red TR, about 75±5% mM citrate, and has a pH of about 5.35±5%.

* * * * *